(12) United States Patent
Zhou et al.

(10) Patent No.: US 10,407,657 B2
(45) Date of Patent: Sep. 10, 2019

(54) VALVE MECHANISM, CELL CULTIVATION APPARATUS USING SAME, AND CELL CULTIVATION METHOD

(75) Inventors: Guangbin Zhou, Tokyo (JP); Takayuki Nozaki, Tokyo (JP); Shizu Matsuoka, Tokyo (JP); Ryota Nakajima, Tokyo (JP); Masaharu Kiyama, Tokyo (JP); Kenichi Minami, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 539 days.

(21) Appl. No.: 14/425,331

(22) PCT Filed: Sep. 5, 2012

(86) PCT No.: PCT/JP2012/072656
§ 371 (c)(1),
(2), (4) Date: Mar. 3, 2015

(87) PCT Pub. No.: WO2014/038024
PCT Pub. Date: Mar. 13, 2014

(65) Prior Publication Data
US 2015/0232798 A1 Aug. 20, 2015

(51) Int. Cl.
*C12M 1/00* (2006.01)
*F16K 7/06* (2006.01)
(Continued)

(52) U.S. Cl.
CPC .......... *C12M 29/00* (2013.01); *A61M 39/285* (2013.01); *C12M 29/06* (2013.01);
(Continued)

(58) Field of Classification Search
CPC ......... C12M 29/00; C12M 29/06; G05D 7/00; Y10T 137/87; F16K 7/063; A61M 39/281; A61M 39/284; A61M 39/285
(Continued)

(56) References Cited

U.S. PATENT DOCUMENTS 3,083,647 A * 4/1963 Muller .................. F04B 43/082
417/474
5,326,033 A 7/1994 Anfindsen
(Continued)

FOREIGN PATENT DOCUMENTS

JP 1-98641 U 6/1989
JP 6-500619 A 1/1994
(Continued)

OTHER PUBLICATIONS

Japanese Office Action received in corresponding Japanese Application No. 2014-534091 dated Nov. 24, 2015.
(Continued)

*Primary Examiner* — Liban M Hassan
(74) *Attorney, Agent, or Firm* — Mattingly & Malur, PC

(57) ABSTRACT

The purpose of the present invention is to provide a valve mechanism which features a simple structure adapted to collectively control the supply of gas or culture medium to a plurality of cultivation containers for simultaneous cultivation and to enhance the reliability of the valve mechanism. The valve mechanism of the invention is a valve mechanism for opening and closing passages for liquid or gas. The valve mechanism includes: clip members adapted to close a plurality of tube passages, respectively; a multiple cam member for opening the clip members in sequence by making contact with the clip members; and a rotational mechanism for rotating the multiple cam member. The clip member includes: a spring for closing a clip thereof; and a clip contact portion for a cam contact portion of the multiple cam member to make contact therewith.

6 Claims, 12 Drawing Sheets

(51) Int. Cl.
*G05D 7/00* (2006.01)
*A61M 39/28* (2006.01)

(52) U.S. Cl.
CPC .............. *F16K 7/063* (2013.01); *G05D 7/00* (2013.01); *A61M 39/281* (2013.01); *A61M 39/284* (2013.01); *Y10T 137/87* (2015.04)

(58) Field of Classification Search
USPC ............ 137/630.17; 251/7; 435/289.1, 317.1
See application file for complete search history.

(56) References Cited

U.S. PATENT DOCUMENTS

| | | | | |
|---|---|---|---|---|
| 5,511,951 | A * | 4/1996 | O'Leary | ............... F04B 43/082 417/474 |
| 5,709,534 | A * | 1/1998 | O'Leary | ............... F04B 43/082 417/474 |
| 5,826,749 | A | 10/1998 | Howland et al. | |
| 6,589,197 | B1 * | 7/2003 | Doi | .......... A61M 1/28 137/862 |
| 6,592,558 | B2 * | 7/2003 | Quah | ................. A61M 39/284 128/912 |
| 6,648,017 | B2 * | 11/2003 | Lamas | ................. A61C 1/0061 137/595 |
| 7,754,478 | B2 | 7/2010 | Suzuki et al. | |
| 2002/0169423 | A1 * | 11/2002 | Zoltan | ................ A61M 39/284 604/250 |
| 2007/0148764 | A1 | 6/2007 | Suzuki et al. | |
| 2009/0143723 | A1 * | 6/2009 | Szpara | .................... A61M 1/28 604/29 |
| 2010/0200706 | A1 * | 8/2010 | Harding | .............. A61M 5/1415 248/62 |

FOREIGN PATENT DOCUMENTS

| | | |
|---|---|---|
| JP | 9-303582 A | 11/1997 |
| JP | 2000-88120 A | 3/2000 |
| JP | 2004-97046 A | 4/2004 |
| JP | 2007-001074 A | 1/2007 |
| JP | 2008-175283 A | 7/2008 |
| JP | 2008-208879 A | 9/2008 |
| JP | 2008-279372 A | 11/2008 |
| JP | 2009-68688 A | 4/2009 |
| JP | 2010-268813 A | 12/2010 |
| WO | 2007/139746 A1 | 12/2007 |

OTHER PUBLICATIONS

Communication Persuant to Article 94(3) EPC received in corresponding European Application No. 12 884 193.9 dated Mar. 20, 2018.

* cited by examiner (A)

(B)

(A)

(B)

(C)

(D)

(A)

(B)

VALVE MECHANISM, CELL CULTIVATION APPARATUS USING SAME, AND CELL CULTIVATION METHOD

TECHNICAL FIELD

The present invention relates to a valve mechanism for opening and closing passage for liquid or gas as well as to a cell cultivation apparatus using the same.

BACKGROUND ART

In cultivation of a variety of cells (suspension cells, adherent cells), it has been a conventional practice to replace nutrient culture medium on a regular basis. Particularly, cultivation of cells having a fast metabolism requires frequent replacement of culture medium. While cell cultivation operations including such a replacement of culture medium have conventionally been performed by experienced operators using pipettes, replacing the culture medium of a large number of cultivation containers involves a great deal of labor. More recently, automated systems for culture medium replacement operation or cultivation operation are actively developed. In such systems, solenoid valves (electromagnetic pinch valves) are commonly employed for open/close control of passages for liquid or gas. However, one solenoid valve is capable of open/close control for only one tube passage. Hence, with increase in the number of tube passages, the number of solenoid valves increases as well. This results in cost increase and complicated open/close control for multiple passages. In a case where a large number of solenoid valves are disposed in an incubator, a fear exists that the unevenness of temperature distribution in the incubator increases due to the influence of heat generated by the solenoid valves. Further, there also is a problem of increase in the cost of solenoid valves because most cultivation environments are at 37° C. in temperature and have a $CO_2$ content of 5% and humidity of 90% or more while the solenoid valves are required of water proof property and sterilization resistance under such environments. Further, the automated cultivation systems are faced with demand for enhanced reliability in the control of tube passages by means of the solenoid.

As a prior-art technique, Japanese Unexamined Patent Application Publication No. Hei 9-303582 discloses "a multiple miniature pinch valve assembly having a structure wherein a plurality of flexible tubes through which a liquid such as chemical agent flows are retained parallel in respective grooves of a tube guide which are arranged in parallel in a lower part of a pinch valve body, a shaft is disposed orthogonally to and above the plural tubes, the shaft has a plurality of cams attached thereto, and the angle of rotation of a motor directly connected to the shaft or connected thereto via a gear or the like is controlled so as to independently open or close the respective tubes by means of the plural cams, and wherein two units including an upper casing part accommodating the cams, shaft and the driving motor therein and the tube guide define a set-in type lock mechanism which is easy to disassemble and assemble" (claim 1).

Further, Japanese Unexamined Patent Application Publication No. 2008-208879 discloses "a pinch valve comprising: a rotary body which can be rotated by a rotary shaft; a pressure member movable in response to the rotation of the rotary body; a guide for movement of the pressure member in a given direction; and a wall disposed at a position opposed to the pressure member in the movable direction of the pressure member, wherein a tube is pressed by the pressure member and the wall and the flow rate of a liquid through the tube is regulated according to the position of the pressure member" (claim 1).

SUMMARY OF THE INVENTION

Technical Problem

The valve mechanisms of the pinch valves set forth in the Japanese Unexamined Patent Application Publication No. Hei 9-303582 and the Japanese Unexamined Patent Application Publication No. 2008-208879 are capable of simultaneous control of the plural tube passages. However, the valve mechanisms are not adapted for simultaneous installation of the plural tube passages and the control thereof, involving problems of complicated structure and the like.

An object of the invention is to provide a rotary valve mechanism which features a simple structure adapted to collectively control the supply of culture medium or gas to a plurality of cultivation containers for simultaneous cultivation and to enhance the reliability of the valve mechanism as well as a cell cultivation apparatus employing the same.

Solution to Problem

For achieving the above object, the invention adopts structures defined by the appended claims, for example. While the present invention includes a plurality of means for solving the above problems, an example of such means is a valve mechanism for opening and closing passage for liquid or gas, which includes: clip members for closing plural tube passages, respectively; a multiple cam member for opening the clip members in sequence by making contact with the clip members; and a rotary mechanism for rotating the multiple cam member.

In the valve mechanism of the invention, it is preferred that the clip member includes a spring for closing a clip, and a clip contact portion for a cam contact portion of the multiple cam member to make contact therewith.

In the valve mechanism of the invention, it is preferred that the multiple cam member includes a rotary shaft, and cam parts including cam contact portions and mounted to the rotary shaft.

A cell cultivation apparatus of the invention includes: the above-described valve mechanism; a plurality of cultivation containers; and tube passages connected to the cultivation containers, respectively, and has a structure wherein the tube passages are opened and closed by the valve mechanism.

Advantageous Effects of the Invention

According to the invention, the valve mechanism features the simple structure adapted to collectively control the supply of culture medium or gas to a plurality of cultivation containers for simultaneous cultivation and to enhance the reliability of the valve mechanism.

DESCRIPTION OF EMBODIMENTS

Figure 1:
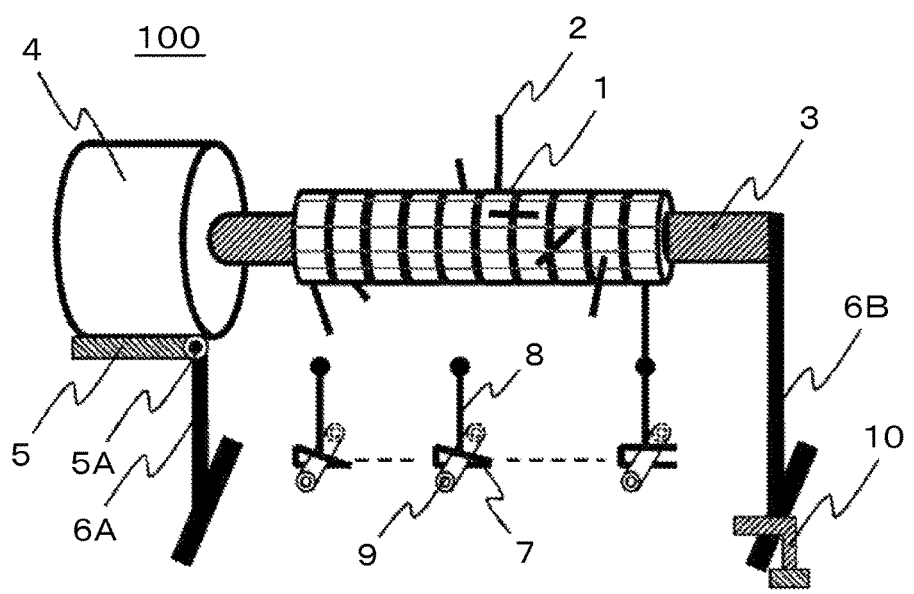
FIG. 1 is a diagram showing an exemplary structure of a valve mechanism according to a first embodiment of the invention.

Embodiments of the invention are described with reference to the accompanying drawings. In all the drawings illustrating the embodiments, like names or reference characters refer to the components of the corresponding function which are explained only once.

First Embodiment

FIG. 1 shows an exemplary structure of a valve mechanism 100 according to a first embodiment of the invention.

In FIG. 1, a character 1 denotes a cam body, a character 2 denoting a cam contact portion, a character 3 denoting a rotary shaft for rotating a multiple cam member, a character 4 denoting a stepping motor. A character 5 denotes a support for the stepping motor 4 and a character 5A denotes a rotary portion of the support 5. Characters 6A, 6B denote a support mechanism for the stepping motor 4 and the rotary shaft 3. A character 7 denotes a clip for closing a tube passage 9. A character 8 denotes a contact portion of the clip 7 which opens the tube passage 9 by making contact with the cam contact portion 2. A character 10 denotes a lock mechanism for locking the support mechanism 6B.

The following description is made on the operating principle of the multiple valve mechanism according to the embodiment shown in FIG. 1. First, cam parts, each including the cam body 1 and the cam contact portion 2, are mounted to the rotary shaft 3 at respective corresponding angles in accordance with an open/close sequence of multiple tube passages. In the case of a 10-channel tube passage, for example, the cam parts are mounted with angle shift of 36° to the rotary shaft. Next, the tube passages 9 are closed by setting the tube passages 9 in respective corresponding clips 7. When setting the tube passages, unlocking the lock mechanism 10 permits the rotary shaft 3 with the multiple cam member to be opened as turned about the rotating part 5A. When the stepping motor 4 connected to the rotary shaft 3 is rotated, a multiple cam mechanism is brought into rotation so as to bring the cam contact portions 2 into contact with the corresponding clip contact portions 8 in sequence. Thus, the clips 7 are opened and the tube passages 9 can be opened with no damage.

Figure 2:
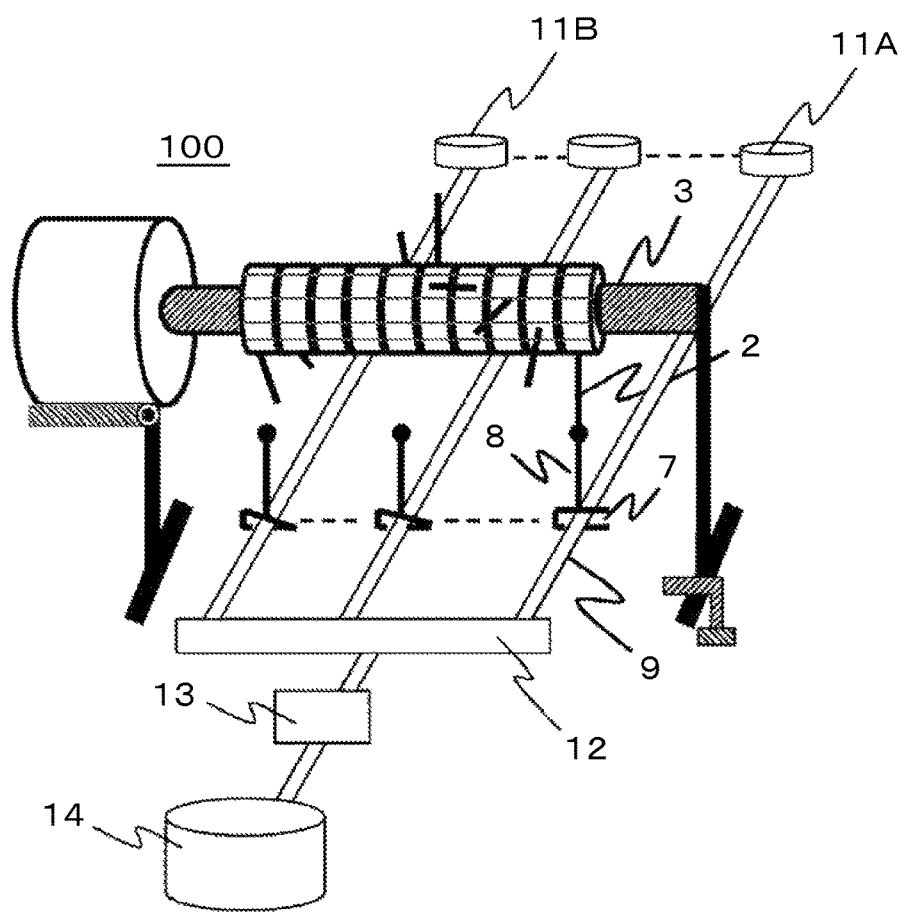
FIG. 2 is a diagram showing a cultivation apparatus employing the valve mechanism according to the first embodiment of the invention.

FIG. 2 shows an example of a cultivation apparatus employing the valve mechanism 100 of FIG. 1. In FIG. 2, characters 11A, 11B denote cultivation containers, a character 12 denoting a passage branch, a character 13 denoting a pump, a character 14 denoting a culture medium tank. Referring to the cultivation apparatus of FIG. 2, description is made on an operation of opening the tube passage channels by means of the valve mechanism of the invention in a case where simultaneous cultivation of cells is performed using the cultivation containers 11. When a culture medium is supplied to the cultivation containers 11, the multiple cam mechanism is rotated while the cam contact portions 2 come into contact with the corresponding clip contact portions 8 in sequence so as to open the clips 7. Thus, the tube passages 9 corresponding to the cultivation containers 11 are opened. Subsequently, the pump 13 is operated to supply the culture medium from the culture medium tank 14 to the cultivation containers 11. The use of the valve mechanism of the invention and the liquid feed pump permits the culture medium to be freely supplied to the individual cultivation containers.

Figure 3:
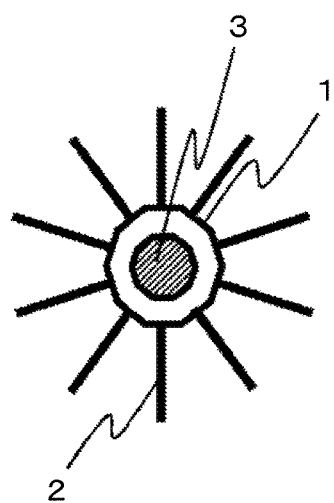
FIG. 3 shows a sectional view of a multiple cam member taken in a direction of a rotary shaft thereof and a sectional view of a cam part.
Figure 3:
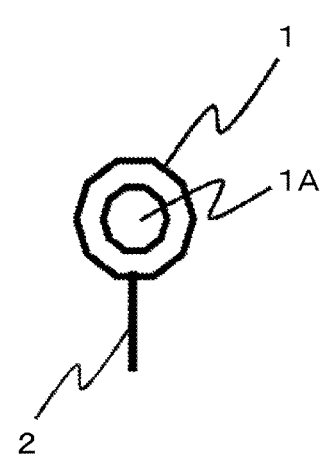

FIG. 3 shows a sectional view (a) of the multiple cam member taken in a direction of the rotary shaft thereof and a sectional view of a single cam part (b). The cam part includes the cam body 1 and the cam contact portion 2. The cam body 1 is formed with a through-hole 1A for insertion of the rotary shaft 3 therethrough. The multiple cam member as shown in the sectional view (a) taken in the direction of the rotary shaft thereof is formed by mounting the cam parts to the rotary shaft with angle shifted by degrees corresponding to the open/close sequence. Angle indexing is facilitated by forming the rotary shaft 3 in a regular polygonal shaft configuration and forming the through-hole 1A in the cam part in a corresponding regular polygonal hole configuration.

In the valve mechanism shown in FIG. 1 and FIG. 2, the cam contact portions 2 of adjoining cam parts are arranged with a given angle shift. An operation of opening and closing the tube passages can be programmed by arranging the individual cam contact portions of the multiple cam member with a predetermined angle shift corresponding to the open/close sequence of the multiple tube passages.

Figure 4A:
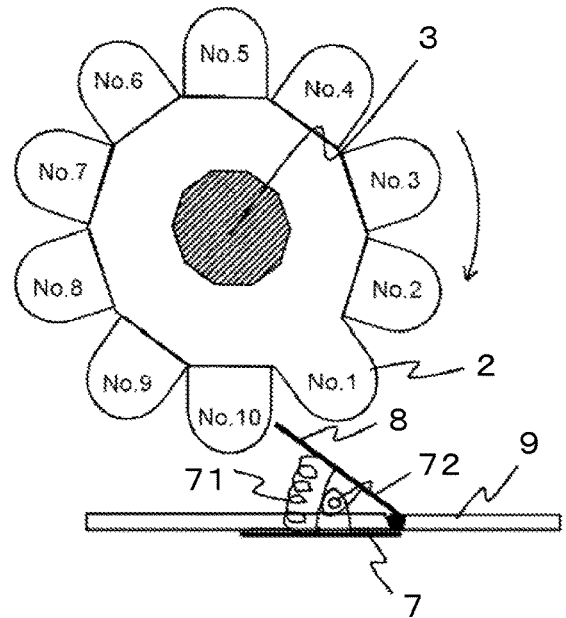
FIG. 4A is a diagram showing a closed state of a clip member according to the invention.
Figure 4B:
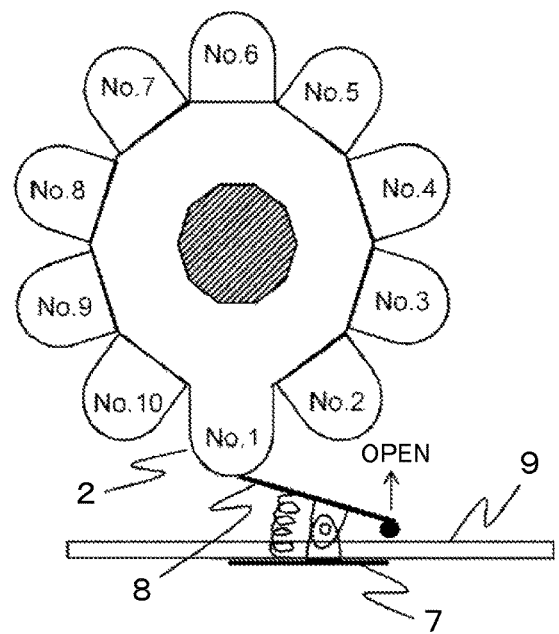
FIG. 4B is a diagram showing an open state of the clip member according to the invention.

FIG. 4A and FIG. 4B are diagrams showing a structure of the clip member according to the invention. FIG. 4A shows a clip close state where the cam contact portion is apart from the clip contact portion. FIG. 4B shows a clip open state where the cam contact portion is in contact with the clip contact portion. In the figures, a character 71 denotes a clip spring, a character 72 denoting a clip rotating portion, a character 8 denoting the clip contact portion. When the replacement of culture medium is not performed, as shown in FIG. 4A, the cam contact portion 2 is apart from the clip contact portion 8 so that the passage tube 9 is closed by the force of the clip spring 71. When the replacement of culture medium is performed, as shown in FIG. 4B, the multiple cam mechanism rotates to bring the cam contact portion 2 into contact with the clip contact portion 8 so that the clip 7 is opened so as to open the tube passage 9.

Figure 5:
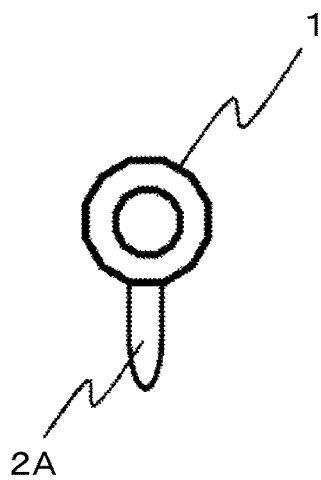
FIG. 5 diagrammatically shows other structures of the cam member according to the invention.
Figure 5:
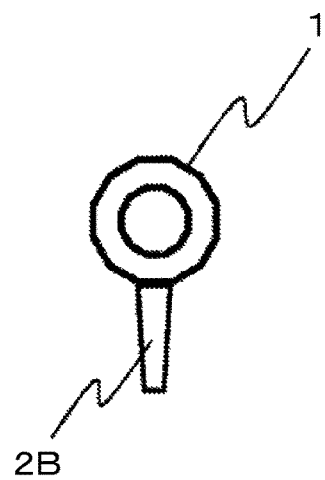
Figure 5:
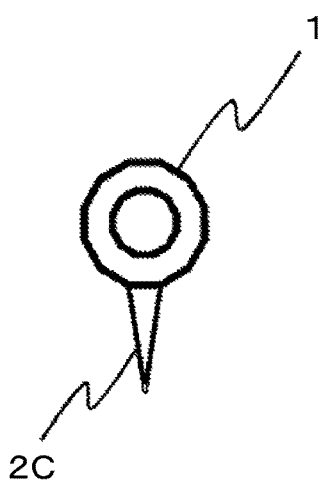
Figure 5:
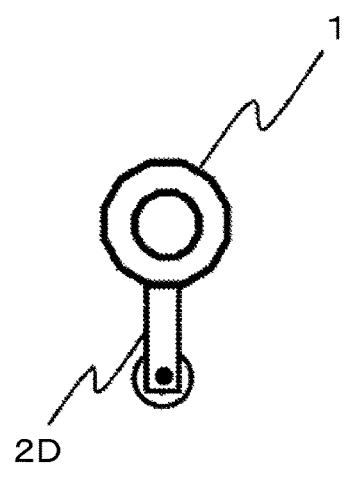

Exemplary modifications of the cam contact portion of the invention are shown in FIG. 5. FIG. 5A shows a cam contact portion, a tip 2A of which is curved to be smooth. FIG. 5B shows a cam contact portion, a tip 2B of which is flattened to be stable. FIG. 5C shows a cam contact portion, a tip 2C of which is sharpened to be precise. FIG. 5D shows a cam contact portion, a tip 2D of which is equipped with a roller to reduce resistance. The tip configuration of the cam contact portion may be properly selected according to the purpose of use.

Since the above-described multiple cam member can be composed of the cam parts of the same structure, the open/close sequence of the tube passages can be easily set by simply mounting the cam parts to the rotary shaft with angle shift as needed. Further, the cam parts, which have the same configuration, are easy to work so that the cost of working can be reduced.

The above-described cam member, clip member and rotary shaft member may preferably use a material having resistance to high humidity and sterilizeability, such as aluminum, stainless steel, resins and the like.

According to the embodiment, the simple structure is adapted to collectively control the supply of culture medium or gas to a large number of cultivation containers for simultaneous cultivation and to enhance the reliability of the valve mechanism.

While this embodiment has been described by way of example of the valve mechanism for tubes (off-passage valve mechanism), the same principle is also applicable to an in-passage valve mechanism.

Second Embodiment

Figure 6:
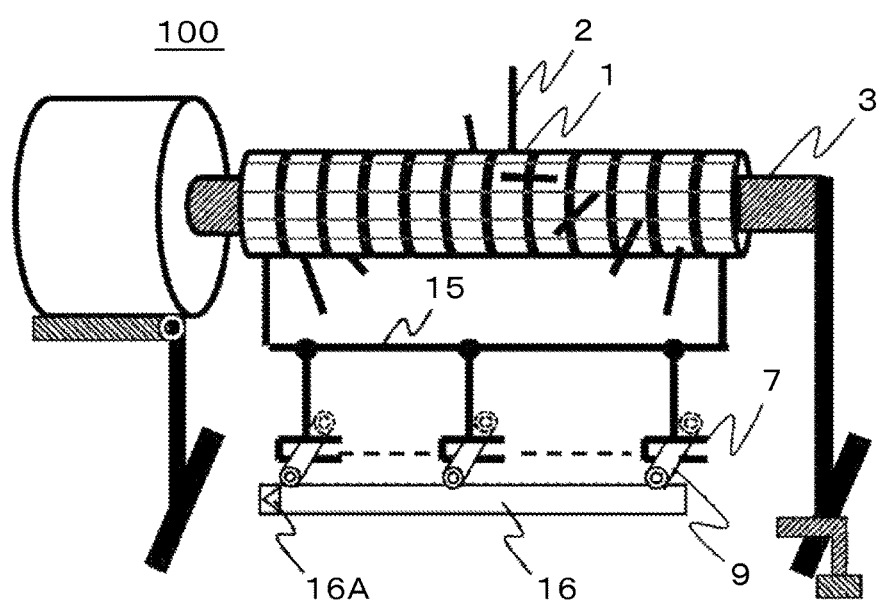
FIG. 6 is a diagram showing an exemplary structure of a valve mechanism according to a second embodiment of the invention.

A valve mechanism according to a second embodiment of the invention is described with reference to FIG. 6.

The second embodiment is constructed the same way as the first embodiment except that the valve mechanism is provided with a tube fixing jig 16 for fixing a plurality of tubes 9 and that the cam mechanism is provided with a rod 15 for simultaneously opening the clips 7.

Figure 7:
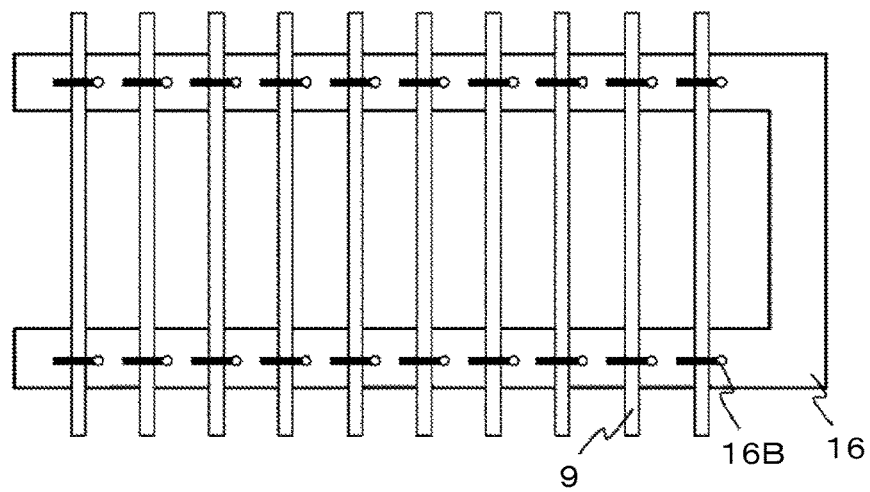
FIG. 7 is a group of diagrams showing an exemplary structure of a tube fixing jig according to the second embodiment of the invention.
Figure 7:
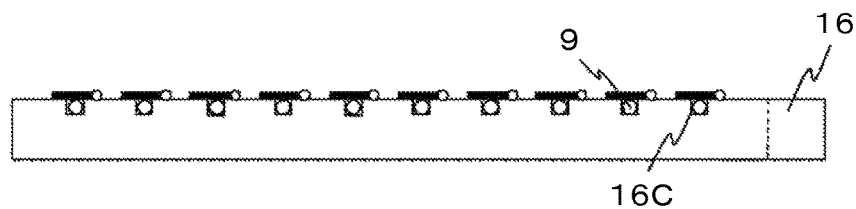

FIG. 7 are diagrams showing a structure of the tube fixing jig 16. FIG. 7A is a top plan view of the tube fixing jig and FIG. 7B is a sectional view thereof. In FIG. 7, a character 16B denotes a tube holder, and a character 16C denotes a tube fixing groove. To fix the passage tube 9 in the fixing jig 16, the passage tube 9 is placed in a tube fixing groove 16C and fixed in position with a tube holder 16B. The use of the fixing jig 16 permits a plurality of tubes to be fixed in position and to be operated simultaneously.

Figure 8A:
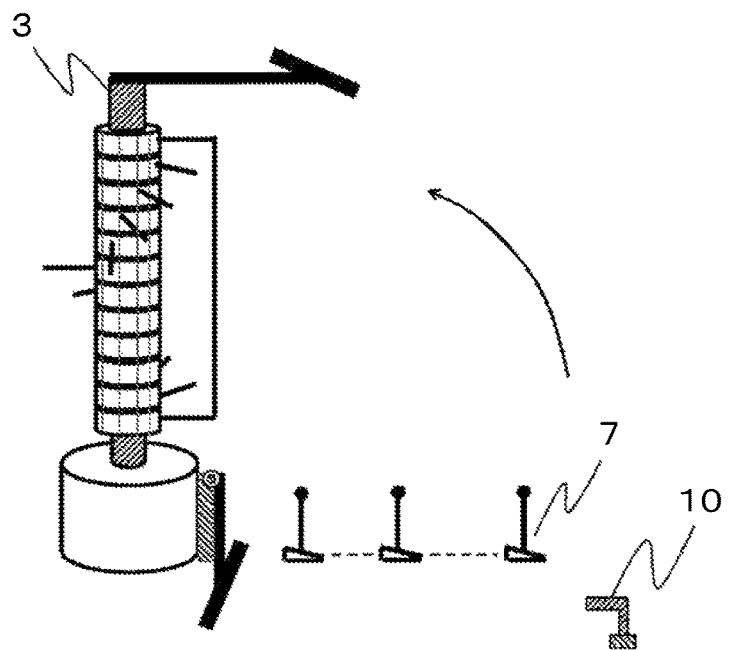
FIG. 8A is a diagram illustrating a movement for mounting tube passages of the valve mechanism according to the second embodiment of the invention.
Figure 8B:
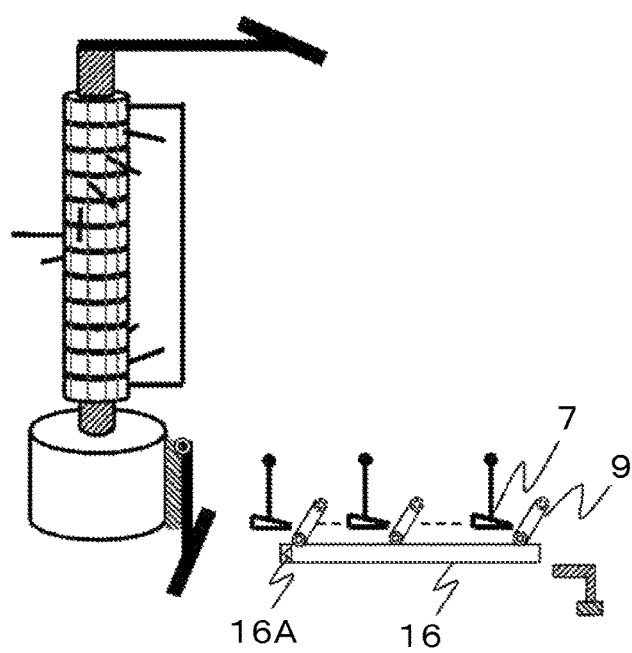
FIG. 8B a diagram illustrating the movement for mounting the tube passages of the valve mechanism according to the second embodiment of the invention.
Figure 8C:
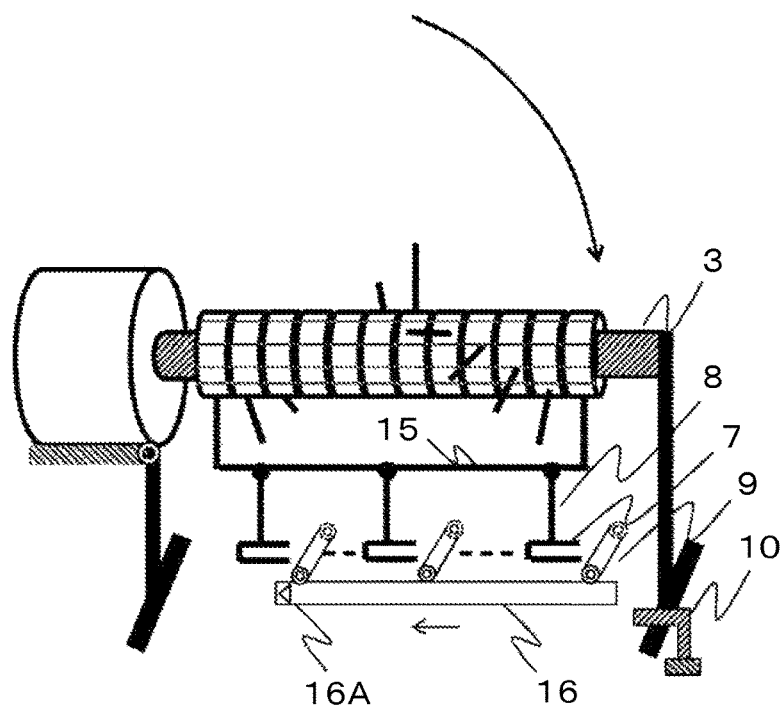
FIG. 8C a diagram illustrating the movement for mounting the tube passages of the valve mechanism according to the second embodiment of the invention.
Figure 8D:
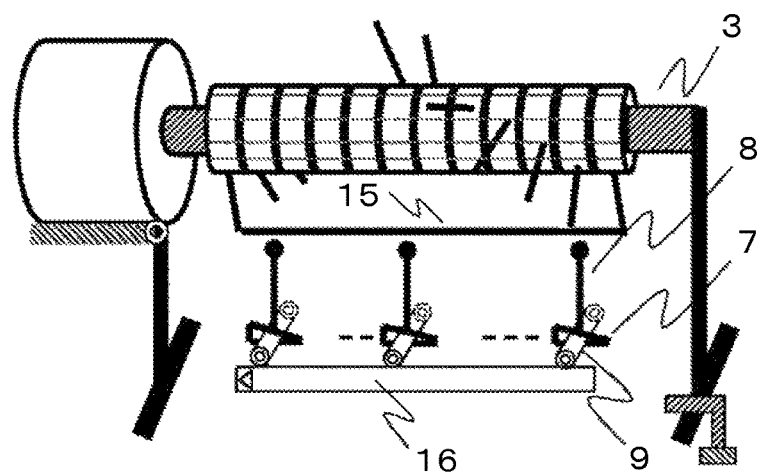
FIG. 8D is a diagram illustrating the movement for mounting the tube passages of the valve mechanism according to the second embodiment of the invention.

In addition to the function of the valve mechanism of the first embodiment, the valve mechanism of this embodiment has a mechanism for simultaneously opening the tube passages of all the channels, and the tube fixing jig for setting a plurality of tube passages in the clips. An operation of setting the tube passages is described with reference to FIG. 8A to FIG. 8D. First, as shown in FIG. 8A, the lock mechanism is unlocked and the rotary shaft 3 is lifted up to increase a distance from the clip member 7. Subsequently, as shown in FIG. 8B, the fixing jig 16 for fixing the tube passages 9 of multiple channels is placed laterally of the individual corresponding clips 7 in a direction indicated by an installation direction mark 16A. Subsequently, as shown in FIG. 8C, the lifted rotary shaft 3 is lowered and returned to the original position, and the lock mechanism 10 is locked. Subsequently, the rotary shaft is rotated to bring the simultaneous opening rod 15 into contact with the clip contact portions 8 of all the channels so as to open all the clips 7. Subsequently, as shown in FIG. 8D, the tube fixing jig 16 is shifted in a direction indicated by the installation direction mark 16A for inserting the tubes 9 in the clips 7, before the rotary shaft 3 is rotated to move the rod 15 away from the clip contact portions 8 and the tube passages of all the channels are closed. Thus, the setting of the tube passages is completed.

An error in setting the tube passages in right sequence can be prevented by using the above-described mechanism and the setting operation. Incidentally, the rod 15 can also be made removable such that the rod 15 may be mounted to the rotary shaft only when the setting of tubes is performed.

In addition to the effect of the first embodiment, this embodiment further provides easy and reliable setting of a large number of passage tubes.

Third Embodiment

A third embodiment features a structure where some of the components of the valve mechanism of the first embodiment are arranged in parallel and adapted to operate in parallel.

Figure 9:
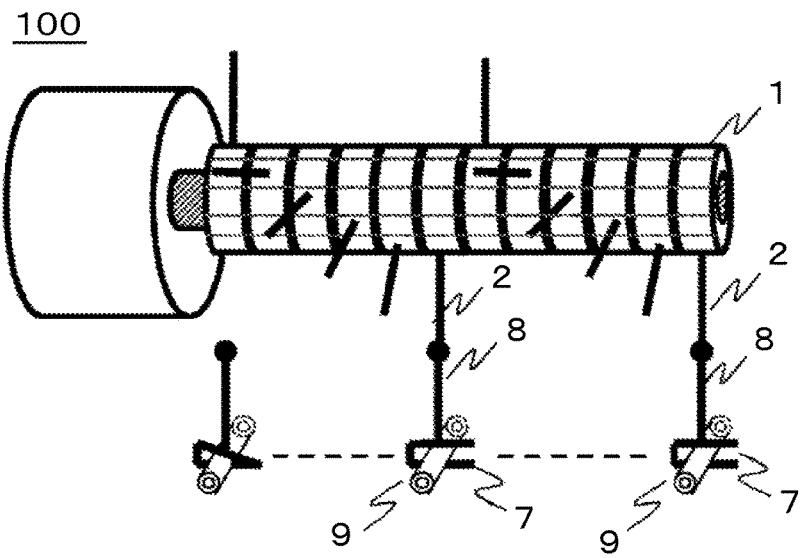
FIG. 9 is a diagram showing another exemplary structure of the valve mechanism according to the invention.

FIG. 9 shows a structure where the multiple cam member of the valve mechanism is divided into a right group and a left group, and the cam contact portions of each group are arranged with a predetermined angle shift corresponding to the open/close sequence of the tube passages 9. As shown in the figure, respective pairs of cam contact portions 2 of the right group and the left group simultaneously come into contact with the clip contact portions 8, thus opening the clips 7 in parallel.

Figure 10:
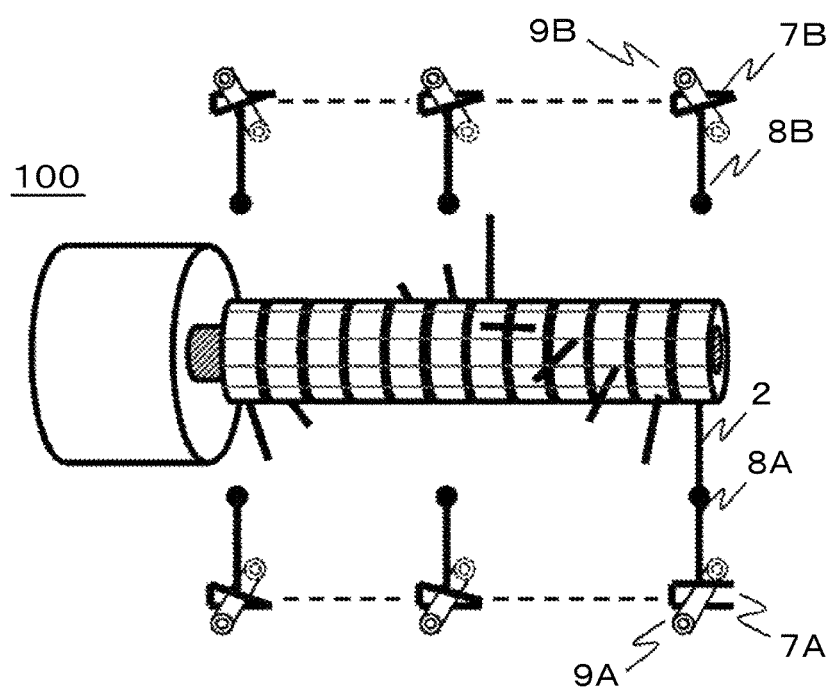
FIG. 10 is a diagram showing another exemplary structure of the valve mechanism according to the invention.

FIG. 10 shows a structure where plural sets of tube passages 9A, 9B and clip members 7A, 7B are made and arranged on the upper and lower sides or on the front and rear sides of the rotary shaft. The use of this valve mechanism enables the collective control of the supply of culture medium or gas to a larger number of cultivation containers.

Figure 11:
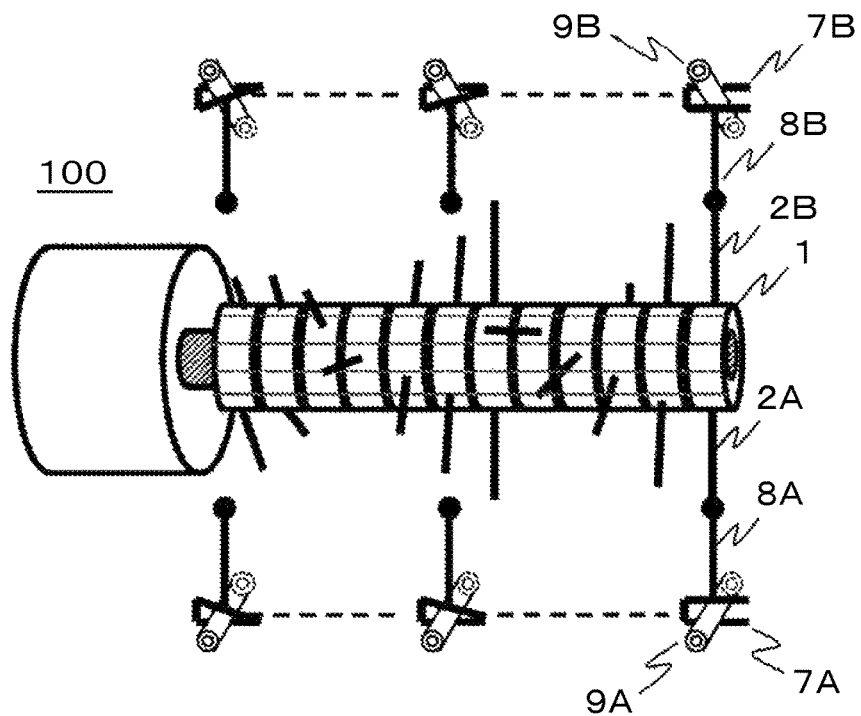
FIG. 11 is a diagram showing another exemplary structure of the valve mechanism according to the invention.

Similarly to FIG. 10, FIG. 11 shows a structure where plural sets of tube passages 9A, 9B and clip members 7A, 7B are made while each of the cam bodies 1 of the multiple cam member is provided with a plurality of cam contact portions 2A, 2B. The use of this valve mechanism enables the collective control of the supply of culture medium or gas to an even larger number of cultivation containers and also enables the parallel opening of the clips 7A, 7B of each set.

Figure 12:
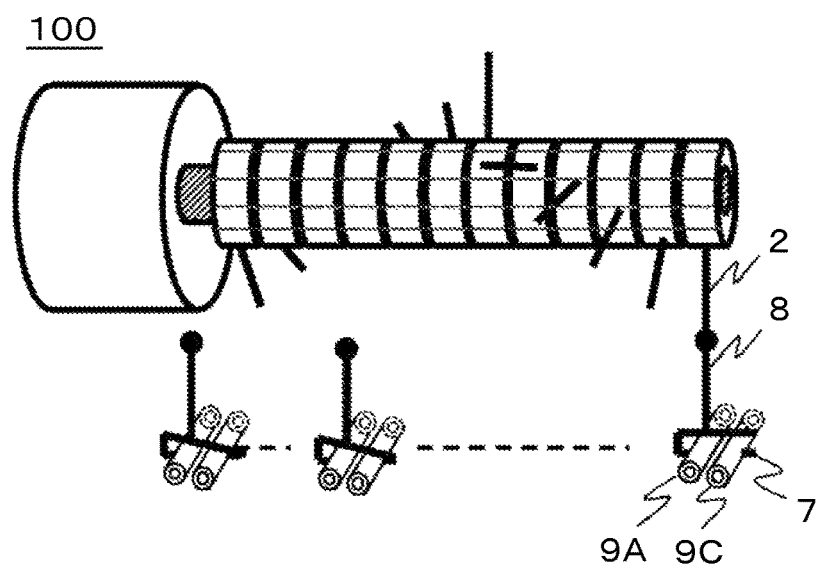
FIG. 12 is a diagram showing another exemplary structure of the valve mechanism according to the invention.

FIG. 12 shows a structure where a single clip member 7 of the valve mechanism of the first embodiment is adapted to set a plurality of tube passages 9A, 9B. For example, a single clip member 7 may be adapted to open and close a feed-side tube passage 9A and an exit-side tube passage 9B connected to a single cultivation container. This valve mechanism can contribute to the size reduction of the required valve mechanism by bringing together the tube passages 9A, 9B in the same open or close state.

Each of the valve mechanisms of the third embodiment can achieve the applicable effects the better with the increase in the number of cultivation containers for simultaneous cultivation.

Fourth Embodiment

Figure 13:
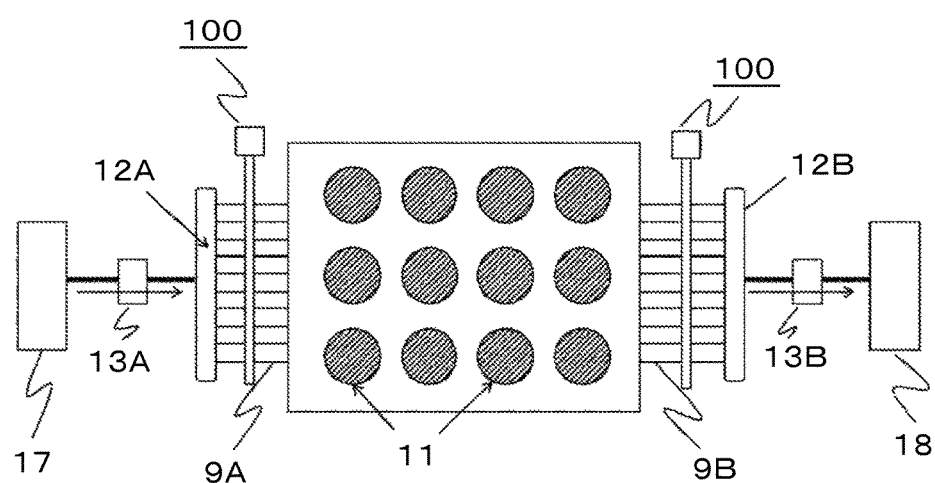
FIG. 13 is a diagram showing an example of a cell cultivation apparatus employing the valve mechanism according to the invention.

A fourth embodiment of the invention relates to a cell cultivation apparatus employing the valve mechanism according to the invention. FIG. 13 shows a cell cultivation apparatus according to the fourth embodiment. The plural cultivation containers 11 are each connected with the feed-side tube passage 9A and the exit-side tube passage 9B. The feed-side tube passage 9A is connected to a feed-side branch portion 12A via the valve mechanism 100. The exit-side tube passage 9B is connected to an exit-side branch portion 12B via the valve mechanism 100. The feed-side branch portion 12A is connected with a feed-side culture medium tank 17 such that fresh culture medium in the feed-side culture medium tank 17 is supplied to the individual cultivation containers 11 by operation of a feed-side pump 13 under the control of the valve mechanism 100. On the other hand, the exit-side branch portion 12B is connected with an exit-side culture medium tank 18 such that stale culture medium from the individual cultivation containers 11 is discharged to the exit-side culture medium tank 18 under the control of the valve mechanism 100. The operation of the valve mechanism 100 is as described in the first embodiment.

As shown in FIG. 13, the cell cultivation apparatus according to this embodiment features a simple structure and an easy open/close control of the passages, providing the supply of fresh culture medium to the large number of cultivation containers and the discharge of stale culture medium from the large number of cultivation containers. As equipped with the valve mechanism of the invention, the apparatus is capable of achieving enhanced reliability in the supply of culture medium or gas and is likely to contribute to an increased success rate of cell cultivation.

It is noted that the present invention is not limited to the above-described embodiments unless the effects of the invention are impaired and other modes that can be contemplated within the technical concept of the invention are construed as being included therein.

1: CAM BODY
1A: THROUGH-HOLE
2, 2A, 2B: CAM CONTACT PORTION
3: ROTARY SHAFT
4: STEPPING MOTOR
5: STEPPING MOTOR SUPPORT PART
5A: ROTATING PART FOR STEPPING MOTOR SUPPORT PART
6A, 6B: SUPPORT MECHANISM
7, 7A, 7B: CLIP MEMBER
71: CLIP SPRING
72: CLIP ROTATING PORTION
8, 8A, 8B: CLIP CONTACT PORTION
9, 9A, 9B, 9C: TUBE PASSAGE
10: LOCK MECHANISM
11, 11A, 11B: CULTIVATION CONTAINER
12, 12A, 12B: FEED-SIDE BRANCH PORTION
13, 13A, 13B: PUMP
14: CULTURE MEDIUM TANK
15: ROD
16: TUBE FIXING JIG
16A: INSTALLATION DIRECTION MARK
16B: TUBE HOLDER
16C: TUBE FIXING GROOVE
17: FEED-SIDE CULTURE MEDIUM TANK
18: EXIT-SIDE CULTURE MEDIUM TANK
100: VALVE MECHANISM

The invention claimed is:

1. A valve mechanism for opening and closing a plurality of passages for liquid or gas, comprising:
 a cam body having a regular polygon shape and extending in an axial direction;
 a rotary shaft inserted through a main axis of the cam body;
 a plurality of cam contact portions disposed on a surface of the cam body and spaced apart by a predetermined angle around the surface of the cam body and extending away from the surface of the cam body;
 a motor connected to one end of the rotary shaft configured to rotate the rotary shaft thereby rotating the cam body;
 a support member supporting the motor disposed below the motor; and
 a plurality of clip members that engage with the plurality of passages, respectively, each clip member having a contact portion disposed at a distal end of the clip member, configured to contact a corresponding cam contact portion,
 wherein upon rotation of the cam body each cam contact portion contacts a corresponding clip member at different times to open the respective passage, and upon contact, the cam contact portions respectively contact the contact portions disposed at the distal end of the clip members,
 wherein the cam body is disposed on a frame having a hinge permitting the cam body to pivot away from the plurality of passages, and
 wherein the hinge is connected to the support member that supports the motor.

2. The valve mechanism according to claim 1, wherein each clip member includes a spring for applying a force to close a clip.

3. The valve mechanism according to claim 1,
 wherein the rotary shaft has a shape having a regular polygonal configuration.

4. The valve mechanism according to claim 1, further comprising:
 a detachable rod having a plurality of arms extending perpendicular to the detachable rod, wherein the plurality of arms are configured to detachably attach the detachable rod to the cam body such that the detachable rod extends parallel with the main axis of the cam body.

5. The valve mechanism according to claim 1, wherein the plurality of cam contact portions are arranged with a predetermined angle shift according to an open/close sequence of the plurality of passages.

6. The valve mechanism according to claim 1, wherein the plurality of cam contact portions or the plurality of clip members are formed of aluminum, stainless steel or a resin material.

* * * * *